United States Patent [19]

Raabe et al.

[11] Patent Number: 4,832,012

[45] Date of Patent: May 23, 1989

[54] INTERMITTENT SIGNAL ACTUATED NEBULIZER

[75] Inventors: Otto G. Raabe, Davis; James I. C. Lee, Sacramento, both of Calif.

[73] Assignee: Vortran Medical Technology, Inc., Sacramento, Calif.

[21] Appl. No.: 71,202

[22] Filed: Jul. 8, 1987

[51] Int. Cl.[4] .............................................. A61M 11/02
[52] U.S. Cl. ............................. 128/200.21; 128/200.17; 128/203.17
[58] Field of Search ................ 128/200.11, 200.14, 128/200.17, 200.21, 200.18, 203.16, 203.17, 203.26, 203.27

[56] References Cited

U.S. PATENT DOCUMENTS

| | | | |
|---|---|---|---|
| 2,466,468 | 5/1949 | Neal | 259/108 |
| 2,774,346 | 12/1956 | Halliburton | 128/200.21 |
| 3,211,433 | 10/1965 | Chrostowski et al. | 259/108 |
| 3,345,047 | 10/1967 | Gooden | 128/200.17 |
| 3,362,404 | 9/1968 | Beasley | 128/145.8 |
| 3,610,237 | 10/1971 | Barkalow et al. | 128/145.8 |
| 3,662,751 | 5/1972 | Barkalow et al. | 128/145.8 |
| 3,724,454 | 4/1973 | Brown | 128/200.21 X |
| 3,744,764 | 7/1973 | Sedam | 259/44 |
| 3,863,630 | 2/1975 | Cavallo | 128/203.27 |
| 3,990,442 | 11/1976 | Patneau | 128/203.16 |
| 4,393,013 | 7/1983 | McMenamin | 261/DIG. 65 X |
| 4,471,773 | 9/1984 | Bunnell et al. | 128/204.21 |
| 4,541,966 | 9/1985 | Smith | 128/200.18 X |
| 4,566,451 | 1/1986 | Badewien | 128/200.21 |

*Primary Examiner*—A. Michael Chambers
*Assistant Examiner*—John C. Fox
*Attorney, Agent, or Firm*—Limbach, Limbach & Sutton

[57] ABSTRACT

A self-contained, high capacity nebulizer, having automatic mixing and temperature control features is provided. The nebulizer may be adapted for use in conjunction with mechanical respirators, ventilators, or breathing machines, and for this purpose will use electrical signals generated by or received from the respirator to automatically control the nebulizing and mixing functions such that nebulization occurs intermittently, that is, only during the inhalation phase of the respiratory function. The nebulizer may also be adapted for manual and/or continuous use by providing an external electrical signal generator to manually control the nebulization and mixing functions.

26 Claims, 3 Drawing Sheets

INTERMITTENT SIGNAL ACTUATED NEBULIZER

TECHNICAL FIELD

The present invention relates to nebulizers for creating medicinal aerosols for inhalation therapy. In particular, the present invention relates to nebulizers used in conjunction with mechanical breathing machines which are used to ventilate the lungs of patients who cannot breathe unaided.

BACKGROUND ART

The thin membrane of the lungs provides an easily penetrated, convenient and generally safe means for obtaining rapid absorption of medication by the body. This is especially desirable where the lungs themselves are diseased or injured. Such medication or drugs are generally delivered to the lung membrane in the form of a fine mist or aerosol which is breathed into the lungs through the nose or mouth of the patient. A variety of devices, called nebulizers by those skilled in the art, have been developed for converting liquids into fine aerosols for this purpose. The simplest of these devices is the hand-held atomizer which converts a liquid to an aerosol when a bulb is compressed to produce a jet of air which atomizes the medication and propels it out of the atomizer. To be effective, the aerosols need to be provided at high concentrations and with droplet size in the respirable range (mass median aerodynamic diameter less than 5 micrometers).

Nebulizers are particularly useful for initiating and continuing respiratory therapy in conjunction with respirators, mechanical ventilators or breathing machines (hereinafter referred to generically as respirators) used to ventilate the lungs of patients having serious respiratory impairment. While some respirators incorporate nebulizers in their design, many do not. Nebulizers incorporated into the structure of such respirators often suffer from many disadvantages. One such disadvantage is severely limited capacity for medication to be nebulized, requiring frequent interruptions in the therapy as new medication is added to the nebulizer reservoir.

Another apparent disadvantage in such existing systems is the lack of a positive means for stirring the medication. This is particularly important to prevent settling when the liquid medication is a suspension. However, such stirring must not be so violent as to create turbulence capable of preventing or destroying nebulization.

Finally, some nebulizers are designed to operate continuously. Obviously this wastes both high pressure gas and medication, since the patient receives a benefit only during the inhalation phase. Those nebulizers which are designed to operate intermittently, i.e. only during the inhalation phase, are generally triggered by the movement of gas through the respirator during inhalation. This results in a slight delay in delivering medication to the patient, since some non-medicated gas will pass into the lungs before the nebulizer begins to operate. Thus, the patient does not receive the maximum possible amount of medication during the inhalation phase.

Most, if not all, such nebulizers are incorporated in respirators in which the inhalation and exhalation phases of the breathing cycle are triggered by changes in air pressure caused by the patient himself. Such "demand" respirators are not useful for patients whose respiratory systems are paralyzed and incapable of causing even slight changes in air pressure. These patients are aided by mechanical respirators in which the phases of the breathing cycle are triggered by electrical signal. There is now no convenient means of treatment for patients on such respirators.

Thus, the need exists for a nebulizer which can be attached to a mechanical respirator, especially those in which the breathing cycle is controlled by an electrical signal, which has a reservoir capacity sufficient to enable several hours of continuous treatment, which can prevent the settling of suspensions or mixtures without creating nebulization-destroying turbulence, and which can deliver medication to the patient just as the inhalation phase of the breathing cycle begins to insure that the patient will receive a maximum amount of medication during the inhalation phase without undue waste.

SUMMARY OF THE INVENTION

The present invention provides a self-contained, high capacity, intermittent nebulizer for use with a mechanical respirator.

In one embodiment, the present invention provides a nebulizer for use with mechanical respirators which use electrical signals to control the breathing cycle. The nebulizer of this embodiment uses the existing electrical signals from the mechanical respirator to synchronize aerosol generation and initiation of the inhalation cycle to insure that a high concentration of respirable aerosol is only provided during the inhalation phase of the breathing cycle. Nebulization is obtained in this embodiment using the premixed oxygen-enriched air provided at high pressure to the respirator. Automatic temperature regulation and stirring of the liquid medication is optionally provided to preclude concentration, separation or settling of the medication ingredients. Finally, a large volume reservoir is provided to eliminate the need for refilling during lengthy treatment protocols.

In another embodiment, the present invention provides a nebulizer with nebulization and mixing functions which uses electrical signals from an external power source to control the nebulization and mixing functions. In this embodiment, manual control of the nebulizer is obtained and can be used to provide medicinal aerosols continuously or on demand.

In yet another embodiment, the present invention provides a method for delivering medicinal aerosols to a user over extended periods of treatment.

BRIEF DESCRIPTION OF THE DRAWINGS

A better understanding of the invention and its advantages will be apparent from the detailed description taken in conjunction with the accompanying drawings in which:

FIG. 3 is a perspective top external view of a nebulizer of the present invention attached to an external power source and signal generator; and, FIG. 4 is a sectional, perspective top view of the nebulizer of FIG. 3.

DETAILED DESCRIPTION OF THE INVENTION

Figure 1:
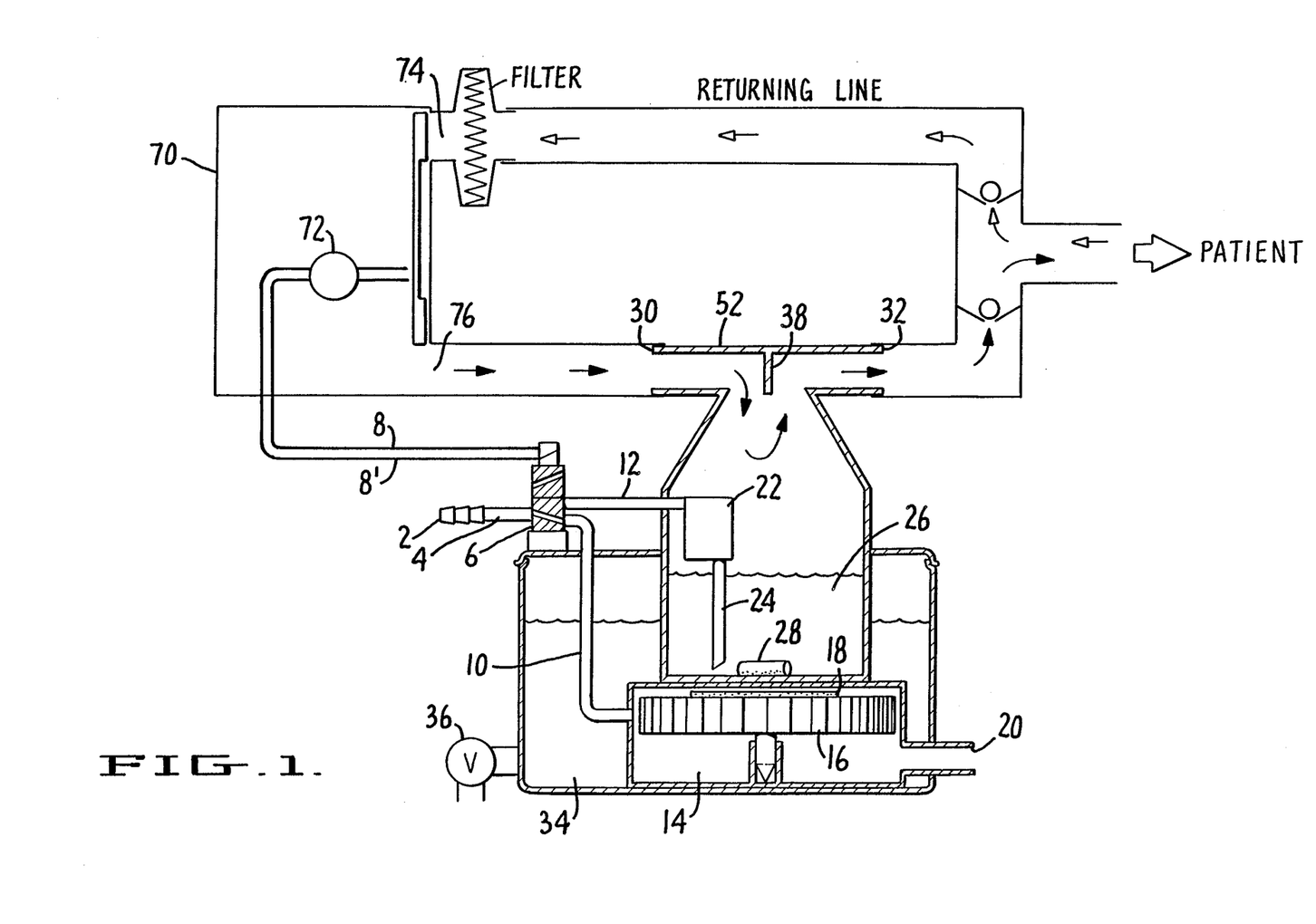
FIG. 1 is a schematic side view a nebulizer of the present invention operationally attached to a mechanical respirator.
Figure 2:
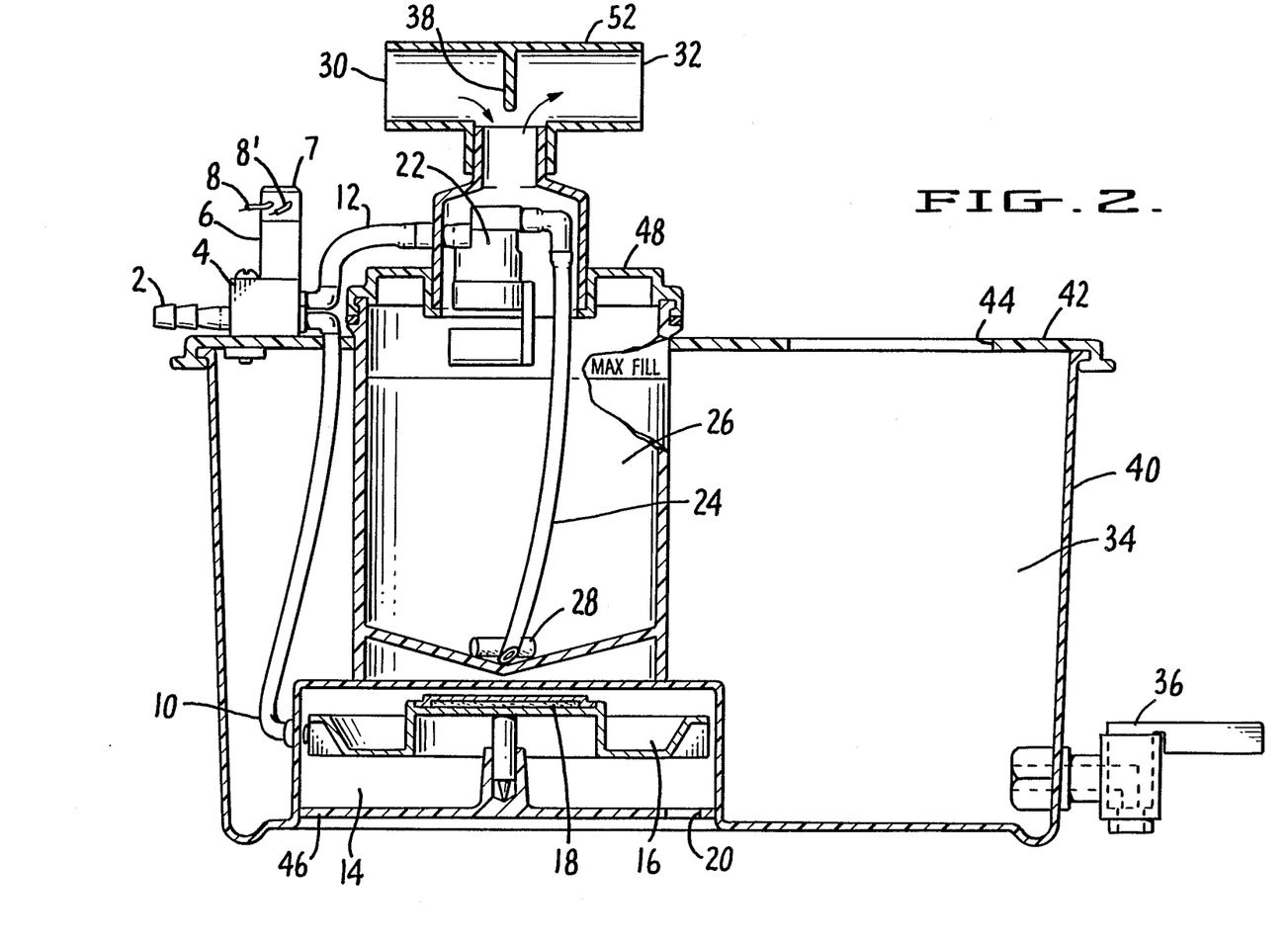
FIG. 2 is a sectional side view of a nebulizer of the present invention.

FIG. 1 shows a nebulizer of the present invention operably connected to a mechanical respirator 70. The nebulizer comprises, in a housing, compressed gas inlet 2, at one end of a compressed gas conduit 4, adapted to be connected to a compressed gas source. Preferably this compressed gas source is the same source which is furnishing oxygen-enriched air to the respirator, and provides compressed air or oxygen mixture to the nebulizer ranging up to about 50 psig.

Compressed gas conduit 4 is connected at the other end to electrically operated nebulizer valve 6. Examples of such valves which have been found useful include the Honeywell Skinner K4M ultraminiature 4-way solenoid operated pneumatic valve and Numatics Mark 3 solenoid operated valves.

Nebulizer valve 6 is connected by electrical lead wires 8, 8' to an electrical signal source 72 on the respirator which controls the inhalation phase of the breathing cycle. Examples of such external electrical signal sources include a respirator solenoid, such as a solenoid actuated inhalation valve, an external electronic monitoring system, or an electronic interface attached to a signal generator on respirator 70, such as an interface connected to a logic circuit in the respirator. The key criteria here is to select an electrical signal source which is synchronized with the breathing cycle of the respirator.

Nebulizer valve 6 also provides the conduits connecting the compressed gas source to turbine conduit 10 and to nebulizer conduit 12. Nebulizer valve 6 switches between two positions as electrical on/off signals are received. In the first position, during inhalation when the electric signal is "on", a passageway is opened between compressed gas conduit 4 and nebulizer conduit 12, and turbine conduit 10 is sealed off. In the second position, during exhalation when the electric signal is "off", a passageway is opened between compressed gas conduit 4 and turbine conduit 10, and nebulizer conduit 12 is sealed off. If desired, the effect of these signals could be reversed.

Turbine conduit 10 terminates, at its other end, in one end of chamber 14 which houses a rotating turbine 16 on top of which is mounted magnet 18. At the other end of chamber 14 is an exhaust conduit 20.

Nebulizer conduit 12 is attached, at its other end, to aerosol transducer 22, which includes liquid feed tube 24 extending into reservoir 26. Reservoir 26 includes magnetic stirring bar 28 which is located in the bottom of the reservoir. The liquid medicine contained in reservoir 26 is preferably kept at constant temperature by temperature bath 34. Alternatively, bath 34 may be changed or drained through spigot 36. The nebulizer is attached to respirator 70 at respirator input conduit 30 and at nebulizer output conduit 32.

The operation of this nebulizer in conjunction with a mechanical respirator 70 is illustrative of the many advantages it has over prior art nebulizers. Compressed gas, ranging up to about 50 psig, is provided continuously to the nebulizer unit through compressed gas inlet 2. This compressed gas may be premixed and enriched with oxygen.

When mechanical respirator 70 begins the inhalation phase of the respiratory cycle, its electrical signal source 72 switches to the "on" position as the respirator exhalation port 74 closes and the respirator inhalation port 76 opens. This signal is simultaneously picked up by nebulizer valve 6, which is attached to electrical signal source 72 by electrical leadwires 8, 8', and switches nebulizer valve 6 to the first position, opening a passageway between compressed gas conduit 4 and nebulizer conduit 12. The flow of compressed gas through turbine conduit 10 into chamber 14 ceases, stopping the stirring action of magnetic stirring bar 28 in reservoir 26. Compressed gas flows through compressed gas conduit 4, nebulizer conduit 12 and into aerosol transducer 22 which converts liquid medicine in reservoir 26 into an aerosol having droplets with a mass median aerodynamic diameter less than about 5 micrometers. The aerosol is generated into the airspace above reservoir 26. At essentially the same time, compressed gas passes into the respirator and enters the nebulizer through respirator input 30. Immediately upon entering the nebulizer, the compressed gas stream encounters wall 38 which deflects the air stream down into the airspace above reservoir 26, where it picks up the aerosol droplets and carries them through nebulizer output 32 and back into the mechanical respirator, and finally into the patient. Thus, even the air which initially enters the patient at the start of the inhalation phase will pass through the nebulizer and carry the medicinal aerosol.

When mechanical respirator 70 begins the exhalation phase of the respiratory cycle, its electrical signal source 72 switches to an "off" position, the respirator inhalation port 76 closes, and the respirator exhalation port 74 opens. Simultaneously, this external electrical signal is received by nebulizer valve 6 through electrical leadwires 8, 8', and the nebulizer valve 6 switches to its second ("off") position, opening a passageway between compressed gas conduit 4 and turbine conduit 10. The compressed gas enters chamber 14 where it encounters the fins or vanes attached to air-driven turbine 16 and moves them, rotating turbine 16. On top of rotating turbine 16 is mounted magnet 18 which exerts a magnetic force, causing magnetic stirring bar 28 in reservoir 26 to spin, stirring the liquid in reservoir 26. The compressed gas flows out of chamber 14 to the atmosphere through exhaust conduit 20.

FIG. 2 shows a cross-sectional view of a nebulizer of the present invention. Housing 40 can be constructed from plastic, metal or any other material suitable for holding a liquid temperature bath. Temperature bath 34 can be either cold or hot. Many methods are known for bringing such baths to and maintaining them at generally constant temperatures by those skilled in the art. For example, by using an ice water bath, the medicine in reservoir 26 can be maintained at 32 degrees F. (0 degrees C.). A temperature bath 34 having a temperature greater than ambient air temperature can be obtained by applying sufficient heat to the exterior surface of housing 40 or by inserting a thermostatically controlled heating element through opening 44 in housing cover 42 to bring the liquid bath to and maintain it at the desired temperature.

A means for draining temperature bath 34 is preferably provided. This can be accomplished in many ways. One such way is shown in FIG. 2 where a rotatable spigot 36 is provided in the bottom of housing 40 such that when spigot 36 is in an open position, a passageway to the outside of housing 40 is opened, permitting any liquid in temperature bath 34 to drain, and such that when spigot 36 is in a closed position, the passageway to the outside of housing 40 is sealed off.

Chamber 14 may be incorporated into a hollow recess in the bottom of housing 40. In this embodiment, air turbine 16 can be rotatably mounted on plate 46 which is attached to the sides of the hollow recess as shown in FIG. 2. Magnet 18 may be attached to the top of turbine 16, or may be molded into the top of turbine 16 as shown in FIG. 2. In this embodiment, when compressed gas is delivered to turbine conduit 10, the gas enters chamber 14 and encounters the vanes of air turbine 16, and causes the turbine 16 and the magnet 18 to rotate. The compressed gas stream then exits chamber 14 in any one of many ways. For example, plate 46 may have a single exhaust conduit 20, as shown in FIGS. 1 and 2, or may be perforated to permit the exhaust of the compressed gas stream from chamber 14.

As noted in the description of FIG. 1 above, compressed gas is continuously supplied to nebulizer valve 6 through compressed gas inlet 2 and compressed gas conduit 4. Compressed gas conduit 4 ends at nebulizer valve 6, which contains a connector 7 for receiving electrical leadwires 8, 8' from a respirator signal source. Nebulizer valve 6 switches between two positions as electrical signals are received from the respirator signal source through leadwires 8, 8'. In the first position, nebulizer valve 6 opens a passageway between compressed gas conduit 4 and nebulizer conduit 12 and seals off turbine conduit 10. In the second position, nebulizer valve 6 opens a passageway between compressed gas conduit 4 and turbine conduit 10, sealing off nebulizer conduit 12.

Turbine conduit 10 and nebulizer conduit 12 can be constructed of any material capable of channeling compressed gas. Preferably, however, they will be constructed from plastic tubing which is removably attached to permit easy cleaning and sterilization of the parts of the nebulizer unit after use, and to permit the removal of reservoir cover 48 to allow access to the interior of the reservoir. Many ways are known by those skilled in the art for providing such removable attachments. For example, a nipple, like that shown for the compressed gas inlet 2 in FIG. 2, having an outside diameter slightly larger than the inside diameter of the plastic tubing used to form the conduits can be used. Because the wall of the plastic tubing is somewhat elastic, it can be forced over the end of such a nipple and will be frictionally held in position on the nipple until a sufficient force is exerted to pull it off the nipple. Generally, the force exerted by the compressed gas in the range used in this unit will not be sufficient to detach the tubing. However, a person pulling on the tubing can easily detach and reattach the tubing. Such a removable attachment can be used in any desired location.

Reservoir 26 is contained within housing 40 in a separate, and preferably removable, container. Reservoir 26 can be constructed of any material suitable for holding and dispensing medicine, such as plastic, stainless steel or glass. Further the reservoir may be constructed to be sterilizable, and hence reusable, or constructed to be disposable after one use. The size of reservoir 26 is limited only by the size of the housing 40. Preferably, reservoir 26 is of a size capable of holding at least 250 ml of liquid. This size permits up to 6 hours of operation before refilling or replacement of medication is necessary. Finally, the bottom of reservoir 26 may be sloped slightly to permit liquid feed tube 24 to drain essentially all of the liquid medication during use.

Reservoir cover 48 is removably attached to the top of reservoir 26 to seal the reservoir off from the atmosphere during operation of the nebulizer unit, to allow access to reservoir 26, and to provide a means for attaching the nebulizer unit to the respirator. Thus, the respirator input 30, nebulizer output 32, and wall 38 can be conveniently provided in respirator adapter 52 which can be integral with or removably attached to reservoir cover 48. Aerosol transducer 22 with attached liquid feed tube 24 are preferably attached to reservoir cover 48.

Magnetic stirring bar 28 may be of any size or material which will cooperate with the force exerted by magnet 18 to provide a stirring action when turbine 16 is rotated by compressed gas. Magnetic stirring bar 28 is preferably coated with an inert coating, such as Teflon, which permits easy sterilization and avoids any reaction with the liquid medicine.

Figures 3, 4:
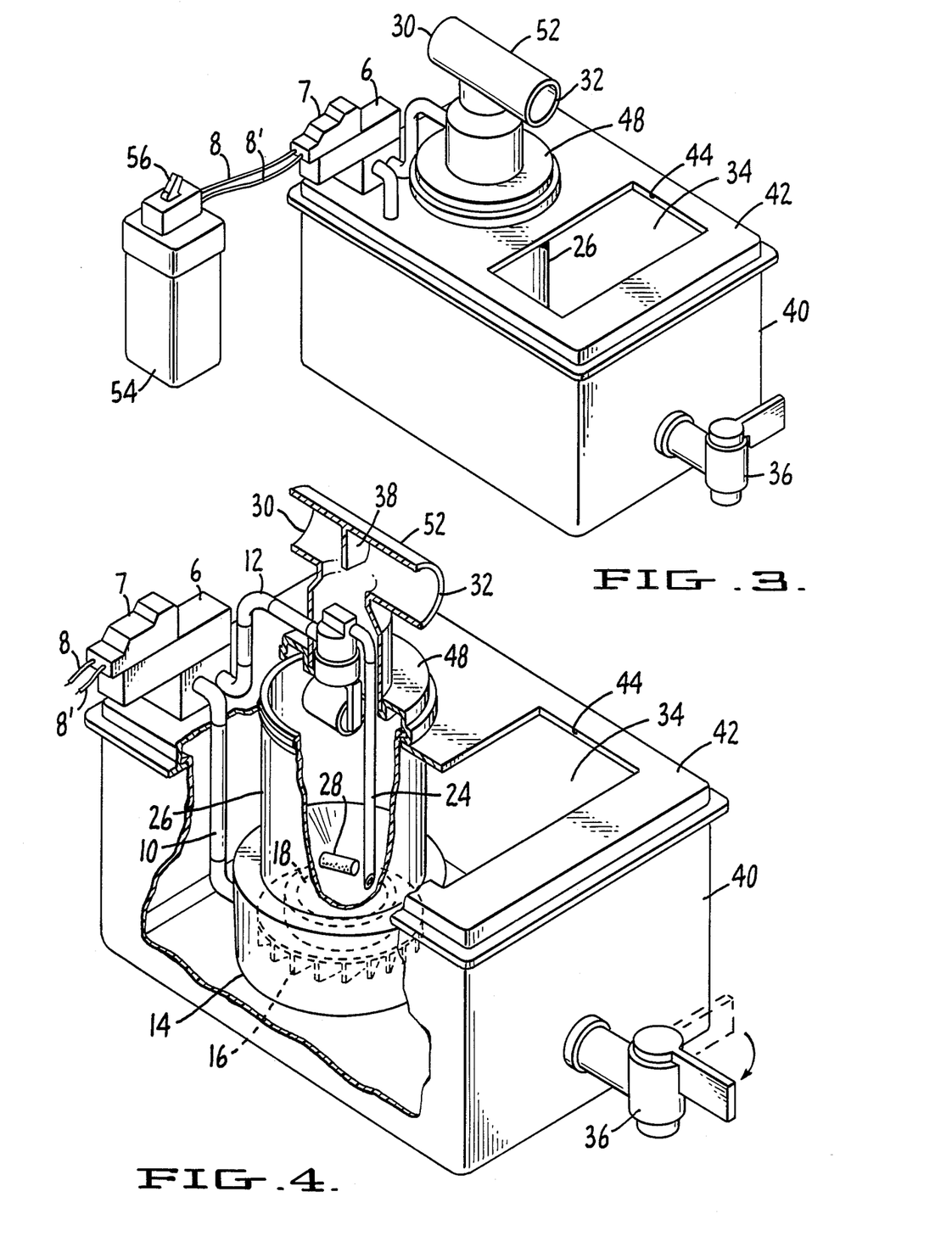

FIGS. 3 and 4 show a perspective exterior and sectional view of a nebulizer unit essentially as described above in FIG. 2. FIG. 3 shows spigot 36 in the closed position. In this position, the passageway from the inside of housing 40 to the outside through spigot 36 is closed and any liquid in temperature bath 34 cannot drain from housing 40. FIG. 4 shows spigot 36 in the open position. In this position, the passageway from the inside of housing 40 to the outside through spigot 36 is open and any liquid in temperature bath 34 can drain from housing 40.

The nebulizer unit is attached to an existing respirator by connecting respirator adapter 52 to the respirator hose carrying compressed air and/or oxygen mixture to the patient, and by using electrical lead wires 8, 8' to connect the nebulizer unit to the electrical signal source on the respirator which is synchronized to the breathing cycle Thus, when the signal source is "off", nebulizer valve 6 switches to the second position and a passageway is opened allowing compressed gas to flow through turbine conduit 10. As discussed above, this rotates an air turbine mounted magnet in chamber 14, causing magnetic stirring bar 28 to spin, mixing the liquid in reservoir 26. This built-in mixing capability provides uniform nebulization of, for example, suspensions, colloids and liposomes in aqueous preparations over extended periods. While other mixing means are known and can be used, magnetic mixing as disclosed herein is preferred because the compressed gas can be used in conjunction with an air turbine, eliminating the need for an external power supply for the mixing function. Further, magnetic mixing is preferred because it thoroughly mixes without causing potential nebulization-destroying turbulence which may result when compressed gas is used directly to agitate the solution.

When the external electrical signal source is "on", nebulizer valve 6 switches to its first position, closing the passageway to turbine conduit 10 and opening the passageway to nebulizer conduit 12. This allows compressed gas to flow into aerosol transducer 22, nebulizing the liquid being drawn up through liquid feed tube 24 by Venturi vacuum, and filling the upper regions of reservoir cover 48 with the aerosol. As compressed gas passes into the nebulizer unit through respirator input 30, it is deflected downward by wall 38, picks up the aerosol and exits through nebulizer output 32, whereit passes back into the respirator and is inhaled by the patient.

As shown in FIG. 3, it is also possible to adapt the present invention to manual use with or without a respirator, by attaching electrical lead wires 8, 8' to an external means for generating electrical signals, such as a battery 54 and switch 56. In this embodiment, a technician or a user can initiate nebulization by placing switch 56 in an "on" position. In this embodiment, the nebulizer may continuously nebulize the liquid medication in reservoir 26 until switch 56 is placed in an "off" position. Obviously, any external electrical power source having appropriate voltage will work in conjunction with a switch. Where the external voltage is not appropriate, an interface which will step down or step up the voltage to an appropriate level can be used. However, a battery is most useful in situations where portability is important or where an appropriate external source of power is not available.

As yet another alternative, the nebulizer of the present invention can be used in the manual mode without any power source or signal souce at all, by using a manual valve, rather than a solenoid actuated valve, to switch from the mixing function to the nebulizing function and back again.

One skilled in the art will recognize at once that it would be possible to construct the various components of the present invention from a variety of materials and to modify the process in a variety of ways. While the preferred embodiment has been described in detail and shown in the accompanying drawings, it will be evident that various further modifications are possible without departing from the scope of the invention as embodied in the claims.

We claim:

1. A method for providing a medicinal aerosol for inhalation by a patient which uses a single source of compressed gas to generate the medicinal aerosol and an electrical signal source to control the generation of said medicinal aerosol, said method comprising the steps of:
   directing said compressed gas to a valve means;
   directing an electrical signal from said electrical signal source to said valve means to place said valve means in a first position such that a passageway is opened between said compressed gas and said nebulizing means, permitting said compressed gas to produce said medicinal aerosol;
   directing said medicinal aerosol to a location where it can be inhaled by said user; and,
   directing an electrical signal from said electrical signal source to said valve means to place said valve means in a second position such that a passageway is opened between said compressed gas and a rotating stirring means, rotating said stirring means to mix said liquid medicine.

2. The method of claim 1 in which said electrical signal can be "on" or "off", such that when said electrical signal is "on" said valve means is placed in said first position and such that when said electrical signal is "off" said valve means is placed in said second position.

3. The method of claim 1 in which said electrical signal can be "on" or "off", such that when said electrical signal is "on" said valve means is placed in said second position and such that when said electrical signal is "off" said valve means is placed in said first position.

4. A nebulizer for use with a mechanical respirator having an inhalation phase, an exhalation phase, and a single source of compressed gas, said nebulizer comprising:
   a housing containing a reservoir for holding liquid medicine to be nebulized;
   a magnetic stirrer comprising a movable magnet located outside of said reservoir and a magnetic stirring bar located inside said reservoir which cooperates with and is moved by the movement of said movable magnet;
   a means for nebulizing said liquid medicine;
   a gas flow means for directing said single source of compressed gas to said stirrer and said means for nebulizing;
   a valve means for directing the flow of gas from said single source for compressed gas to either said stirrer or said means for nebulizing through said gas flow means and for synchronizing the flow of said gas to said means for nebulizing only during said inhalation phase of said mechanical respirator by sensing an electrical signal generated by the mechanical respirator; and,
   a means for attaching said housing to said mechanical respirator such that when said means for nebulizing is operative the gas from said mechanical respirator will pass through the nebulizer and carry the nebulized medicine to the patient.

5. The nebulizer of claim 4 in which said magnetic stirrer comprises:
   a magnetic stirring bar located within said reservoir; and,
   a magnet mounted on air-powered turbine operatively mounted outside said reservoir such that when said compressed gas moves said turbine and said magnet, said magnetic stirring bar will move inside said reservoir.

6. The nebulizer of claim 4 in which said valve means uses said electrical signal such that when said respirator switches to an inhalation mode, a passageway is opened between said single source of compressed gas and said means for nebulizing, and such that when said repirator switches to an exhalation mode, a passageway is opened between said single source of compressed gas and said stirrer.

7. The nebulizer of claim 6 in which said valve means alternately controls said first means and said second means such that said first means will not be operated concurrently with the operation of said second means.

8. The nebulizer of claim 4 in which said gas flow means comprises a first conduit connected at one end to said stirrer and at the other end to said valve means, and a second conduit connected at one end to said means for nebulizing and at the other end to said valve means.

9. The nebulizer of claim 4 in which said housing additionally comprises a temperature bath for bringing said liquid medicine to, and maintaining said liquid medicine at, a generally constant temperature other than what would be expected without the temperature bath.

10. A method for controlling the generation of a medicinal aerosol for inhalation by a patient using a mechanical respirator having a source of compressed gas for providing a gas stream through the respirator, an inhalation phase and an exhalation phase and capable of generating a first electrical signal during the inhalation phase and a second electrical signal during the exhalation phase, said method comprising the steps of:
   detecting the first electrical signal;
   opening a conduit between the source of compressed gas and a nebulizer containing a liquid medicine to generate the medicinal aerosol for so long as the first electrical signal is detected;
   directing substantially all of the gas stream from the respirator through the nebulizer to carry the medicinal aerosol to the patient to enable inhalation of the medicinal aerosol;

detecting the second electrical signal; and, closing the conduit between the source of compressed gas and the nebulizer to prevent generation of the medicinal aerosol for so long as the second electrical signal is detected.

11. The method of claim 10 additionally comprising the step of directing the compressed gas to a turbine operated mixer for mixing the liquid medicine for so long as the second electrical signal is detected.

12. The method of claim 10 additionally comprising the step of placing the nebulizer in a temperature bath to maintain the temperature of the liquid medicine at a substantially constant temperature other than what would be expected without the temperature bath.

13. A nebulizer adapted to use a source of compressed gas and an external electrical signal source which generates a first and a second electrical signal, said nebulizer comprising:

a housing containing a reservoir for holding liquid to be nebulized;

an aerosol generator for nebulizing the liquid; a gas flow means for directing compressed gas from the compressed gas source to the aerosol generator, the gas flow means including a valve attached to the source of compressed gas and capable of sensing the external electrical signal source and opening a conduit for the flow of gas from the source of compressed gas to the aerosol generator when the first electrical signal is detected and closing the conduit to the aerosol generator when the second electrical signal is detected, in which the external electrical signal is generated by a mechanical respirator having an inhalation phase with a breathing gas flow and an exhalation phase and capable of generating the first electrical signal during the inhalation phase and the second signal during the exhalation phase, such that the generation of aerosol by the nebulizer is synchronized with the inhalation phase of the mechanical respirator and additionally comprising an adapter for attaching the nebulizer to the respirator which enables substantially all of the breathing gas flowing from the respirator to pass through the nebulizer housing during the inhalation phase of the mechanical respirator.

14. The nebulizer of claim 13 additionally comprising a turbine driven mixer attached to the housing for mixing the liquid to be nebulized, and in which the valve means is additionally capable of opening a conduit between the compressed gas source and the turbine driven mixer when the second electrical signal is detected for mixing the liquid to be nebulized.

15. A nebulizer for use with a mechanical respirator having an inhalation phase, an exhalation phase, a source of compressed gas for forming a breathing gas stream, and electrical means for switching between the inhalation phase and the exhalation phase, said nebulizer comprising:

a housing containing a reservoir for holding liquid to be nebulized;

an aerosol generator for nebulizing said liquid;

a valve having a means for sensing electrical signals emitted by the mechanical respirator's electrical means for switching between the inhalation phase and the exhalation phase, the valve being attached to the source of compressed gas for the respirator and capable of opening a first passageway from the compressed gas source when the means for sensing the respirator's electrical signals senses that the inhalation phase is occurring, and capable of closing the first passageway when the means for sensing the respirator's electrical signals senses that the exhalation phase is occurring;

a conduit connecting the valve to the aerosol generator for directing the flow of gas from the first passageway to the aerosol generator; and, a means for attaching the nebulizer housing to the mechanical respirator such that when the inhalation phase occurs, substantially all of the breathing gas stream will be directed from the respirator through the nebulizer for carrying the nebulized liquid to the patient for inhalation.

16. The nebulizer of claim 15 in which the valve is additionally capable of opening a second passageway from the compressed gas source when the means for sensing the respirator's electrical signals senses that exhalation is occurring, and additionally comprising a turbine driven mixer for mixing the liquid to be nebulized and a second conduit connecting the valve to the mixer for directing the flow of gas from the second passageway to the turbine for turning the turbine to cause the mixing of the liquid to be nebulized.

17. The nebulizer of claim 16 in which the turbine driven mixer is a magnetic stirrer comprising a movable magnet located on the turbine outside of the reservoir and a magnetic stirring bar located inside the reservoir which cooperates with and is moved by the movement of said movable magnet as the turbine turns.

18. The nebulizer of claim 15 in which the aerosol generator is an aerosol transducer having a liquid feed tube extending into the reservoir.

19. The nebulizer of claim 15 in which the compressed gas delivered to the nebulizer ranges in pressure up to about 50 psig.

20. The nebulizer of claim 15 in which the housing additionally comprises a temperature bath for bringing the liquid to be nebulized to, and maintaining the liquid to be nebulized at, a generally constant temperature other than what would be expected without the temperature bath.

21. A nebulizer for use with a mechanical respirator having an inhalation phase, an exhalation phase, a source of compressed gas for forming a breathing gas stream, and a means for switching between the inhalation phase and the exhalation phase which generates a first electrical signal synchronized with the inhalation phase and a second electrical signal synchronized with the exhalation phase, said nebulizer comprising:

a housing containing a reservoir for holding liquid to be nebulized;

a rotary mixer for mixing the liquid to be nebulized;

a means for nebulizing the liquid;

a gas flow means for directing compressed gas from the compressed gas source to the means for nebulizing and the rotary mixer, the gas flow means including a valve means capable of detecting the electrical signals generated by the mechanical respirator as it switches from inhalation phase to exhalation phase and capable of opening a first conduit for the flow of gas from the source of compressed gas to the means for nebulizing when the first electrical signal is detected and of closing the first conduit and opening a second conduit between the source of compressed gas and the rotary mixer when the second electrical signal is sensed.

22. The nebulizer of claim 21 in which said rotary mixer is a magnetic stirrer comprising:

a magnetic stirring bar located within said reservoir; and, a magnet mounted on air-powered turbine operatively mounted outside said reservoir such that said compressed gas will rotate said turbine and said magnet, causing said magnetic stirring bar to move inside said reservoir.

23. The nebulizer of claim 21 in which the means for nebulizing is an aerosol transducer having a liquid feed tube extending into said reservoir.

24. The nebulizer of claim 21 in which the compressed gas is delivered to the nebulizer in pressures ranging up to about 50 psig.

25. The nebulizer of claim 21 in which the housing additionally comprises a temperature bath for bringing the liquid to be nebulized to, and maintaining the liquid at, at a constant temperature other than what would be expected without the temperature bath.

26. The nebulizer of claim 21 in which substantially all of the breathing gas stream passing from the mechanical respirator to the patient during the inhalation phase passes through the nebulizer housing.

* * * * *

UNITED STATES PATENT AND TRADEMARK OFFICE
CERTIFICATE OF CORRECTION

PATENT NO. : 4,832,012

DATED : May 23, 1989

INVENTOR(S) : OTTO G. RAABE and JAMES I. C. LEE

It is certified that error appears in the above - identified patent and that said Letters Patent is hereby corrected as shown below:

In the Heading: The following cited U.S. Patent document reference should be added:

3,379,194     4/1973     Ziermann     128/145.6

In the Specification:

Col. 2, line 3 should read:
"breathing cycle are triggered by electrical signal$\underline{s}$. There"

Col. 2, line 58 should read:
"FIG. 1 is a schematic side view $\underline{of}$ a nebulizer of the"

Col. 6, line 34 should read:
"cycle$\underline{.}$"

Col. 6, line 63 should read:
"aerosol and exits through nebulizer output 32, [whereit] $\underline{where\ it}$"

In the Claims:

Claim 6, Col. 8, line 36 should read:
"means for nebulizing, and such tha when said [repirator] $\underline{respirator}$"

Claim 25, Col. 12, line 10 should read:
"at, [at] a constant temperature other than what would be"

Signed and Sealed this

Thirteenth Day of February, 1990

*Attest:*

JEFFREY M. SAMUELS

*Attesting Officer*     *Acting Commissioner of Patents and Trademarks*